United States Patent [19]

Stryer et al.

[11] Patent Number: 5,055,556
[45] Date of Patent: * Oct. 8, 1991

[54] FLUORESCENT CONJUGATES FOR ANALYSIS OF MOLECULES AND CELLS

[75] Inventors: Lubert Stryer, Stanford; Alexander N. Glazer, Orinda; Vernon T. Oi, Menlo Park, all of Calif.

[73] Assignee: The Board of Trustees of the Leland Stanford Jr. Univ., Stanford, Calif.

[*] Notice: The portion of the term of this patent subsequent to May 28, 2002 has been disclaimed.

[21] Appl. No.: 791,248

[22] Filed: Oct. 25, 1985

Related U.S. Application Data

[63] Continuation of Ser. No. 701,324, Feb. 13, 1985, which is a continuation-in-part of Ser. No. 454,768, Dec. 30, 1982, Pat. No. 4,520,110, which is a continuation-in-part of Ser. No. 309,169, Oct. 6, 1981, abandoned.

[51] Int. Cl.$^5$ .................... C07K 15/04; C07K 17/00; G01N 33/566; G01N 33/53
[52] U.S. Cl. .................... 530/370; 530/387; 530/388; 436/501; 436/547; 436/800; 436/805
[58] Field of Search ............... 436/501, 547, 800, 805; 530/370, 387, 388, 389, 807

[56] References Cited

U.S. PATENT DOCUMENTS

| | | | |
|---|---|---|---|
| 4,193,983 | 3/1980 | Ullman et al. | 424/12 |
| 4,302,536 | 11/1981 | Longenecker | 435/7 |
| 4,520,110 | 5/1985 | Stryer et al. | 436/501 |
| 4,542,104 | 9/1985 | Stryer et al. | 436/536 |

OTHER PUBLICATIONS

Eder, J., et al., *Immunochemistry*, vol. 15, 1978 pp. 315-321.
C. OhEocha (1963) Biochemistry 2:375-382.
A. Saha (1962) Chem. Abstracts 57:6493e.
A. Glazer (1972) Chem. Abstracts 76:55529d p. 138.
E. Gantt (1977) Chem. Abstracts 87:180925h p. 321.
Stedman's Med. Dict., Williams and Wilkins, Baltimore, 22nd Ed., 1972, pp. 154, 155, 318, 766, 1004.
R. Aalberse (1973) Clinica Chimica Acta 48:109-111.
C. Hales et al. (1980) Meth. Enzymology 70:334-355.
M. Kronick et al. (1983) Clin. Chem. 29:1582-1586.

*Primary Examiner*—Johnnie R. Brown
*Assistant Examiner*—Jeremy M. Jay
*Attorney, Agent, or Firm*—Bertram I. Rowland

[57] ABSTRACT

Sensitive detection techniques and compositions for such techniques are provided by employing fluorescent proteins having bilin prosthetic groups as labels. The bilin containing proteins can be conjugated to ligands or receptors for use in systems involving ligand-receptor binding for the analysis, detection or separation of ligands and receptors. Particularly, one or more of the bilin containing proteins may be used as labels in conjunction with each other or other fluorescers for defining subsets of naturally occurring aggregations e.g. cells.

4 Claims, 4 Drawing Sheets

HPLC OF PHYCOERYTHRIN-IgG
(a) PE-S-S-IgG
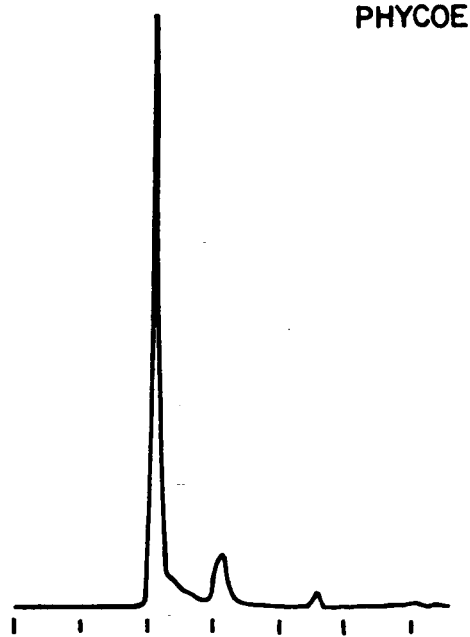
(b) PE-SH
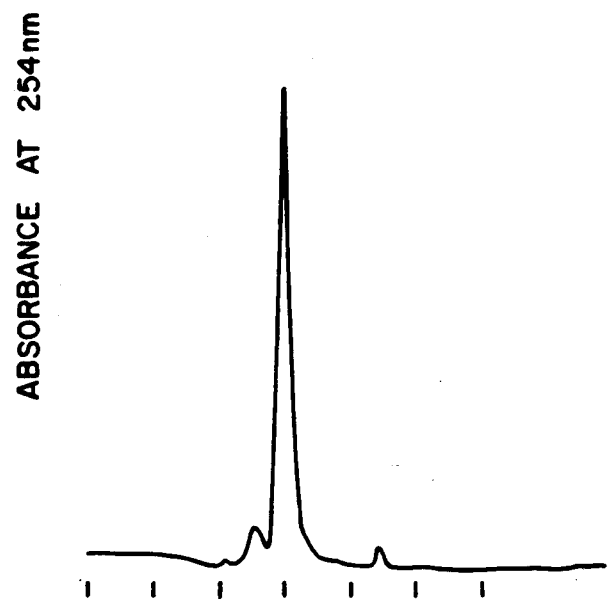
(c) IgG-S-S-Pyr
MINUTES AFTER INJECTION
FIG. — 1

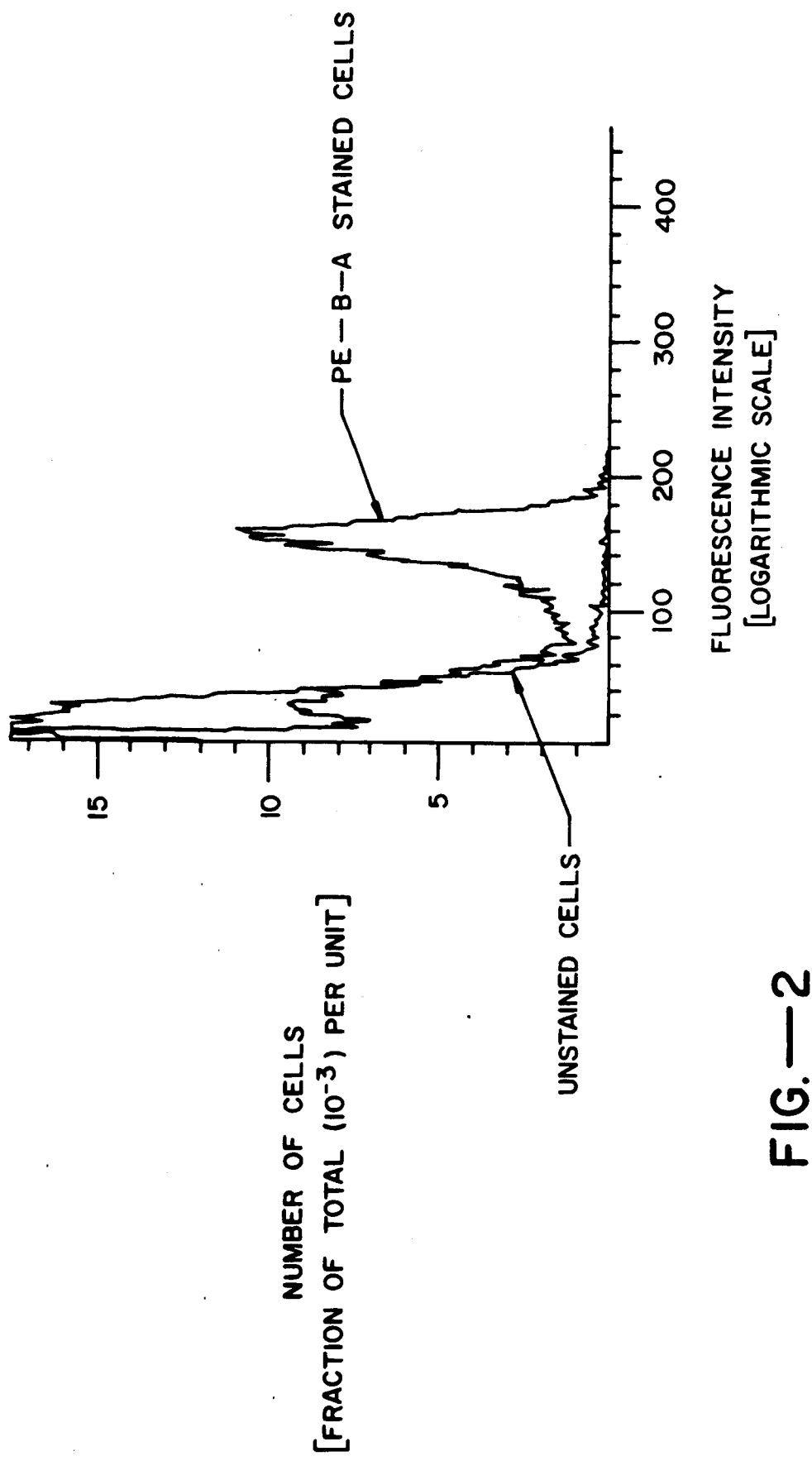
FIG.—2

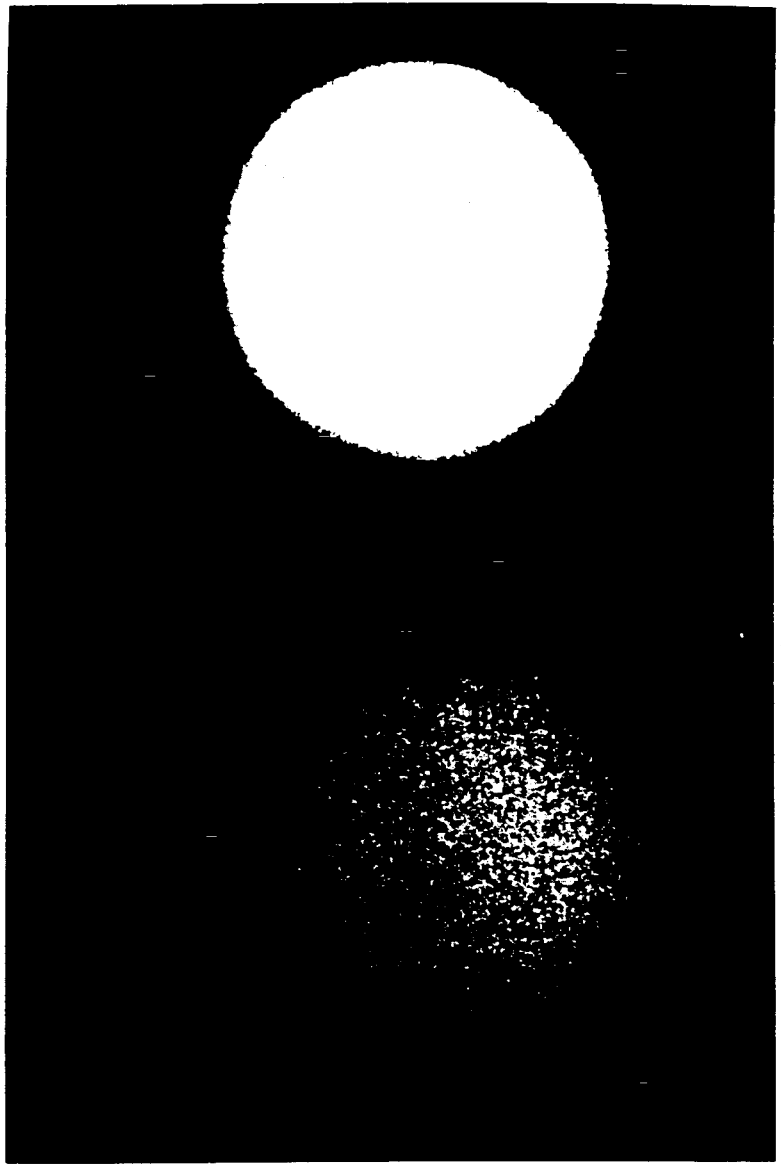
FIG.—3A

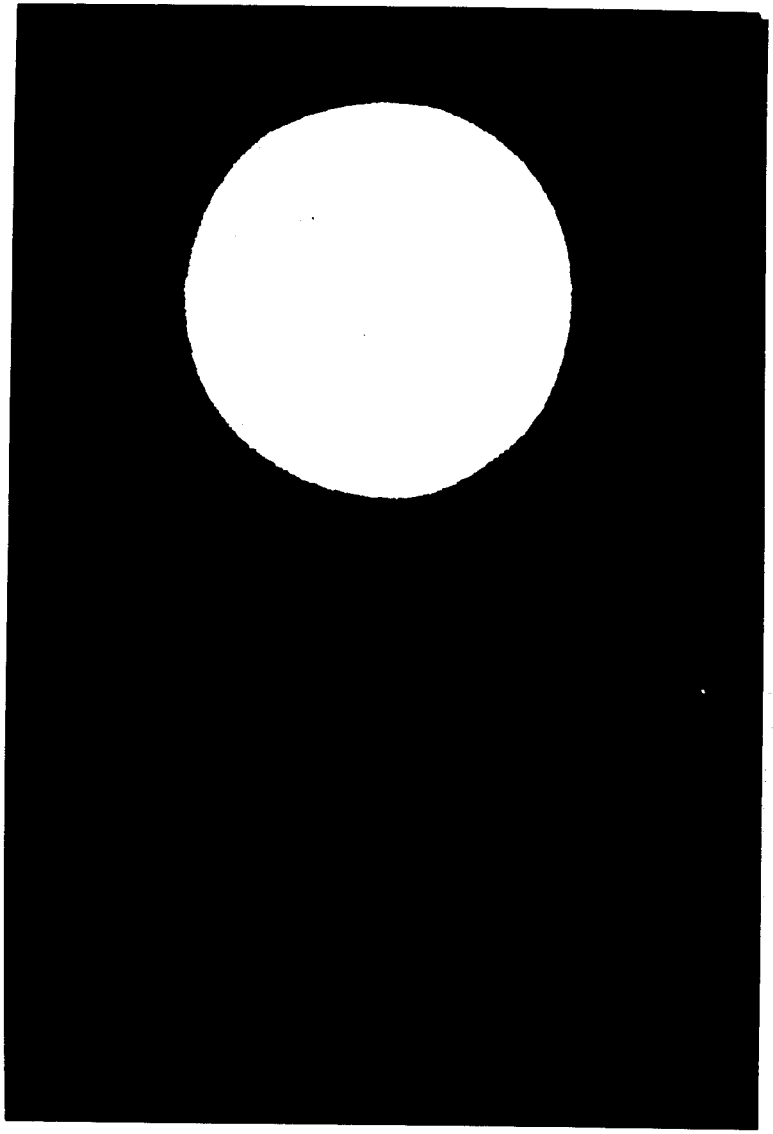
FIG.—3B
PE-B-A
STAINED
BEAD
(ORANGE-RED)

FLUORESCENT CONJUGATES FOR ANALYSIS OF MOLECULES AND CELLS

CROSS-REFERENCE TO RELATED APPLICATIONS

This is a Continuation application of U.S. application Ser. No. 701,324, filed Feb. 13, 1985, which is a Continuation-in-part application of U.S. application Ser. No. 454,768, filed Dec. 30, 1982, now U.S. Pat. No. 4,520,110, issued May 28, 1985, which was a Continuation-in-part application of U.S. application Ser. No. 309,169, filed Oct. 6, 1981, now abandoned.

BACKGROUND OF THE INVENTION

1. Field of the Invention

Fluorescent probes are valuable reagents for the analysis and separation of molecules and cells. Some specific examples of their application are: (1) identification and separation of subpopulations of cells in a mixture of cells by the techniques of fluorescence flow cytometry, fluorescence-activated cell sorting, and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg et al., "Cellular Immunology," 3rd ed., chapt. 22, Blackwell Scientific Publications, 1978 (fluorescence-activated cell sorting); and by Goldman, "Fluorescence Antibody Methods," Academic Press, New York, 1968 (fluorescence microscopy and fluorescence staining).

When employing fluorescers for the above purposes, there are many constraints on the choice of the fluorescer. One constraint is the absorption and emission characteristics of the fluorescer, since many ligands, receptors, and materials associated with such compounds in the sample in which the compounds are found e.g. blood, urine, cerebrospinal fluid, will fluoresce and interfere with an accurate determination of the fluorescence of the fluorescent label. Another consideration is the ability to conjugate the fluorescer to ligands and receptors and the effect of such conjugation on the fluorescer. In many situations, conjugation to another molecule may result in a substantial change in the fluorescent characteristics of the fluorescer and in some cases, substantially destroy or reduce the quantum efficiency of the fluorescer. A third consideration is the quantum efficiency of the fluorescer. Also of concern is whether the fluorescent molecules will interact with each other when in close proximity, resulting in self-quenching. An additional concern is whether there is non-specific binding of the fluorescer to other compounds or container walls, either by themselves or in conjunction with the compound to which the fluorescer is conjugated.

The applicability and value of the methods indicated above are closely tied to the availability of suitable fluorescent compounds. In particular, there is a need for fluorescent substances that emit in the longer wavelength visible region (yellow to red). Fluorescein, a widely used fluorescent compound, is a useful emitter in the green. However, the conventional red fluorescent label rhodamine has proved to be less effective than fluorescein. The impact of this deficiency is felt in the area of fluorescence-activated cell sorting. The full potential of this powerful and versatile tool has not yet been realized because of limitations in currently available fluorescent tags. Two and three-parameter fluorescence sorting have not been effectively exploited, largely because of the unavailability of good long wavelength emitting probes.

Other techniques, involving histology, cytology, immunoassays would also enjoy substantial benefits from the use of a fluorescer with a high quantum efficiency, absorption and emission characteristics at longer wavelengths, having simple means for conjugation and being substantially free of non-specific interference.

SUMMARY OF THE INVENTION

Proteins with bilin prosthetic groups are employed as fluorescent labels in systems involving ligand-receptor reactions. The biliproteins are readily conjugated, provide for high quantum efficiency with absorption and emission at long wavelengths in the visible, and enhance the sensitivity and accuracy of methods involving ligand-receptor reactions. The biliproteins may be used individually, in combination, or together with non-proteinaceous fluorescers.

BRIEF DESCRIPTION OF THE DRAWINGS

FIG. 1 shows the high pressure liquid chromatograms of FIG. 1(a) phycoerythrin-immunoglobulin conjugate (PE-S-S-IgG) and the reactant precursors thereof, FIG. 1(b) thiolated phycoerythrin (PE-SH) and FIG. 1(c) activated immunoglobulin (IgG-S-S-Pyr).

FIG. 2 shows the fluorescence-activated cell sorter analysis of a cell population containing spleen cells bearing PE-B-A stained anti-IgG immunoglobulin.

FIG. 3a shows the visualization of a mixture of agarose beads containing a labeled anti-immunoglobulin by fluorescence microscopy utilizing standard fluorescein emission filter combinations, wherein some beads were labeled with PE-B-A and some beads were labeled with fluorescein-avidin.

FIG. 3b shows the visualization of the same cell population as in FIG. 3a under fluorescence microscopy utilizing a red filter combination.

DESCRIPTION OF THE SPECIFIC EMBODIMENTS

Compositions are provided comprising biliproteins, (the term "biliproteins" is equivalent to the term "phycobiliproteins") conjugated to a member of a specific binding pair, said pair consisting of ligands and receptors. These compositions find use for labeling by non-covalent binding to the complementary member of the specific binding pair. A wide variety of methods involve competitive or non-competitive binding of ligand to receptor for detection, analysis or measurement of the presence of ligand or receptor. Many of these techniques depend upon the presence or absence of fluorescence as a result of non-covalent binding of the labeled member of the specific binding pair with its complementary member.

The conjugates of the subject invention are biliproteins bound either covalently or non-covalently, normally covalently, to a particular ligand or receptor. The biliproteins have a molecular weight of at least about 30,000 d, (d-daltons) more usually at least about 40,000 d, and may be as high as 600,000 or more daltons usually not exceeding about 300,000 d.

The biliproteins will normally be comprised of from 2 to 3 different subunits, where the subunits may ranged from about 10,000 to about 60,000 molecular weight. The biliproteins are normally employed as obtained in their natural form from a wide variety of algae and cyanobacteria. The presence of the protein in the biliproteins provides a wide range of functional groups for conjugation to proteinaceous and non-proteinaceous molecules. Functional groups which are present include amino, thio and carboxy. In some instances, it may be desirable to introduce functional groups, particularly thio groups where the biliprotein is to be conjugated to another protein.

Depending upon the nature of the ligand or receptor to be conjugated, as well as the nature of the biliprotein, the ratio of the two moieties will vary widely, where there may be a plurality of biliproteins to one ligand or receptor or a plurality of ligands or receptors to one biliprotein. For small molecules, that is, of molecular weight less than 2,000 d, there will generally be on the average at least one and not more than about 100, usually not more than about 60 conjugated to a biliprotein. With larger molecules, that is at least about 2,000 molecular weight, more usually at least about 5,000 molecular weight, the ratio of biliproteins to ligand or receptor may vary widely, since a plurality of biliproteins may be present in the conjugate or a plurality of the specific binding pair member may be present in the conjugate. In addition, in some instances, complexes may be formed by covalently conjugating a small ligand to a biliprotein and then forming a specific binding pair complex with the complementary receptor, where the receptor may then serve as a ligand or receptor in a subsequent complex.

The ligand may be any compound of interest for which there is a complementary receptor. For the most part, the ligands of interest will be compounds having physiological activity, either naturally occurring or synthetic. One group of compounds will have molecular weights in the range of about 125 to 2,000, more usually from about 125 to 1,000, and will include a wide variety of drugs, small polypeptides, vitamins, enzyme substrates, coenzymes, pesticides, hormones, lipids, etc. These compounds for the most part will have at least one heteroatom, normally chalcogen (oxygen or sulfur) or nitrogen and may be aliphalitic, alicyclic, aromatic, or heterocyclic or combinations thereof. Illustrative compounds include epinephrine, prostaglandins, thyroxine, estrogen, corticosterone, ecdysone, digitoxin, aspirin, pencillin, hydrochlorothiazide, quinidine, oxytocin, somatostatin, diphenylhydantoin, retinol, vitamin K, cobalamin, biotin and folate.

Compounds of greater molecular weight, generally being 5,000 or more molecular weight include poly(amino acids)-polypeptides and proteins-polysaccharides, nucleic acids, and combinations thereof e.g. glycosaminoglycans, glycoproteins, ribosomes, etc. Illustrative compounds include albumins, globulins, hemogloblin, surface proteins on cells, such as T- and B-cells e.g. Leu, Thy, Ia, tumor specific antigens, α-fetoprotein, retinol binding protein, C-reactive protein, enzymes, toxins, such as cholera toxin, diphtheria toxin, botulinus toxin, snake venom toxins, tetrodotoxin, saxitoxin, lectins, such as concanavalin, wheat germ agglutinin, and soy bean agglutinin, immunoglobulins, complement factors, lymphokines, mucoproteins, polysialic acids, chitin, collagen, keratin, etc.

Depending upon the molecule being labeled, a wide variety of linking groups may be employed for conjugating the biliprotein to the other molecule. For the most part, with small molecules, those under 2,000 molecular weight, the functional group of interest for linking will be carbonyl, either an aldehyde to provide for reductive amination or a carboxyl, which in conjunction with carbodiimide or as an activated ester e.g. N-hydroxy succinimide, will form a covalent bond with the amino groups present in the biliprotein; a thio ether or disulfide, where the biliprotein may be modified with an activated olefin and a mercapto group added or activated mercapto groups joined e.g. Ellman's reagent; isothiocyanate; diazonium; nitrene or carbene. Where the biliproteins are conjugated with a protein, various bifuctional reagents may be employed, such as dialdehydes, tetrazolium salts, diacids, or the like, or alternatively, one or both of the two proteins involved may be modified for conjugation to the other protein, for example, a mercapto group may be present or be introduced on one protein and an activated olefin e.g. maleimide introduced onto the other protein.

There is ample literature for conjugating a wide variety of compounds to proteins. See for example A. N. Glazer, *The Proteins*, Vol. IIA, 3rd Ed., N. Neurath and R. L. Hill, eds., Academic Press, pp. 1-103 (19760; A. N. Glazer et al., "Chemical Modification of Proteins," *Laboratory Techniques in Biochemistry and Molecular Biology*, Vol. 4, PRT I, T. S. Work and E. Work, eds., North-Holland Publishing Co. (1975); and K. Peters et al., *Ann. Rev. Biochem.*, 46, 423-51 (1977), the descriptions of which are incorporated by reference herein. Examples of commercially available cross-linking reagents are disclosed in the Pierce 1981-82 Handbook and General Catalog, pp. 161-166, Pierce Chemical Co., Rockford, Ill.

Known linking procedures as described in the above publications may be employed. For example, the phycobiliprotein may be reacted with iminothiolane, thereby placing an accessible sulfhydryl group thereon. The other component of the conjugate may be activated by reaction with succinimidylpyridylthiopropionate. Mixture of the two prepared components of the conjugate results in joining thereof through disulfide bonds. Alternatively, instead of employing succinimidyl-pyridylthiopropionate, the protein may be reacted with m-maleimidobenzoyl N-hydroxysuccinimide ester, and the resulting conjugate combined with the sulfhydry modified protein to form a thioether.

As previously indicated, instead of having a covalent bond between the specific binding pair member of interest and the biliprotein, non-covalent bonds may be employed. For example, if one wishes to conjugate a biliprotein to avidin, biotin may be covalently conjugated to the biliprotein through its carboxyl group, and the resulting biotinylated biliprotein combined with avidin, whereby a biliprotein labeled avidin will result.

As already indicated, biliproteins are naturally occurring compounds which may be found in a wide variety of sources and even individual sources may have more than one biliprotein.

Examples of phycobiliproteins useful in the present invention are allophycocyanin, phycocyanin, phycoerythrin, allophycocyanin B, B-phycoerythrin, phycoerythrocyanin, and b-phycoerythrin. The structures of phycobiliproteins have been studied and their fluorescent spectral properties are known. See A. N. Glazer, "Photosynthetic Accessory Proteins with Bilin Prosthetic Groups," *Biochemistry of Plants*, Volume 8, M. D. Hatch and N. K. Boardman, EDS., Academic Press, pp. 51-96 (1981), and A. N. Glazer, "Structure and Evolution of Photosynthetic Accessory Pigment Systems with Special Reference to Phycobiliproteins," *The Evolution of Protein Structure and Function*, B. S. Sigman and M. A. Brazier, EDS., Academic Press, pp. 221-244 (1980). The spectroscopic properties, including fluorescence emission maxima, of some common phycobiliproteins are shown below in Table 1.

TABLE 1

SPECTROSCOPIC PROPERTIES OF PHYCOBILIPROTEINS

| Biliprotein | Distribution[1] | Absorption maxima in the visible[2] (nm) | Fluorescence emission maximum[2] (nm) |
|---|---|---|---|
| Allophycocyanin B | C,R | 671 > 618 | 680 |
| Allophycocyanin | C,R | 650 | 660 |
| C-Phycocyanin | C,R | 620 | 637 |
| R-Phycocyanin | R | 617 > 555± | 636 |
| Phycoerythrocyanin | C | 568 > 590(s) | 607 |
| C-Phycoerythrin | C | 565 | 577 |
| b-Phycoerythrin | R | 545 > 563(s) | 570 |
| B-Phycoerythrin | R | 545 > 563 > 498(s) | 575 |
| R-Phycoerythrin | C,R | 567 > 538 > 498 | 578 |

[1] C = cyanobacteria; R = red algae.
[2] For a given biliprotein, the exact positions of the absorption and emission maxima vary somewhat depending on the organism that serves as the source of the protein and on the method of purification.

Of particular interest are biliproteins having absorption maxima of at least about 450 nm, preferably at least about 500 nm, having Stokes shifts of at least 15 nm, preferably at least about 25nm, and having fluorescence emission maxima of at least about 500 nm, preferably at least about 550 nm. The subject conjugates may be used in a wide variety of ways, enhancing known methodologies for the detection, diagnosis, measurement and study of antigens, either present as individual molecules, or in more complex organizations, such as viruses, cells, tissue, organelles e.g. plastids, nuclei, etc.

One of the uses of the subject conjugates is in fluorescent staining of cells. The cells may then be observed under a microscope, the presence of the fluorescer being diagnostic of the presence of a specific determinant site or the cells may be used in a fluorescence activated cell sorter (FACS). One or more of the biliproteins may be used, where the fluorescence emission maximum of the biliproteins is separated by at least about 15 nm, preferably by at least about 25 nm. Alternatively, the biliproteins may be used in conjunction with fluorescers other than biliproteins, for examples fluorescein, dansyl, umbelliferone, benzoxadiazoles, pyrenes, rose bengal, etc., where the emission maxima are separated by at least about 15 nm, preferably at least about 25 nm.

By using combinations of fluorescers, one can provide for the detection of subsets of aggregations, such as particular types of cells, strains of organisms, strains of viruses, the natural complexing or interaction of different proteins or antigens, etc. Combinations of particular interest are combinations of fluorescein with biliproteins capable of being activated with the same laser light source. That is, biliproteins which have absorption maxima in the range of about 450 to 500 nm e.g. phycoerythrin.

Another use of the subject biliproteins is in immunoassays or competitive protein, binding assays, where the subject biliproteins serve as fluorescent labels. Here, the biliprotein may be conjugated to either a ligand or a receptor, particularly an antibody. While for the most part the antibodies will be IgG, other antibodies such as IgA, IgD, IgE and IgM may also find use. In addition, various naturally occurring receptors may be employed, particularly receptors having high binding specificity, such as avidin. By biotinylating either the receptor, the biliprotein or both, one can link various molecules through avidin. A wide variety of fluorescent assays are known. A few of these assays are illustrated in U.S. Pat. Nos. 3,998,943; 3,985,867; 3,996,345; 4,036,946; 4,067,959; 4,160,016 and 4,166,105, the relevant portions of which are incorporated herein by reference.

The biliproteins have many favorable properties. (1) they have very high absorption coefficients in the longer wavelength visible spectral region; (2) they have high fluorescence quantum yields; (3) they are stable proteins and have good storage stability; (4) they are highly soluble in aqueous solutions; (5) the biliprotein unit can readily be coupled to a wide range of biologically specific molecules; (6) they do not bind non-specifically to cells. The fluorescence of biliprotein-biomolecule conjugates is more than thirty times as intense as that of fluorescein conjugates, on a molar basis. The long wavelength emitting fluorescent conjugates of the present invention have an additional advantage over shorter wavelength emitters. Most biomolecules in cells and body fluids do not absorb and emit in the red end of the visible spectrum. Consequently, biliprotein conjugates are less subject to interference by endogenous biomolecules than are shorter wavelength emitting conjugates. Furthermore, it is easier to work in the red end of the spectrum rather than in the ultraviolet region because plastic materials do not absorb and emit in the yellow to red spectral region.

The following examples are offered by way of illustration and not by way of limitation.

EXPERIMENTAL

EXAMPLE 1

As an example of a fluorescent conjugate of the invention, a phycoerythrin-immunoglobulin conjugate was prepared. Thiolated phycoerythrin (PE-SH) was prepared by the addition of 2-iminothiolane to phycoerythrin. Activated immunoglobulin (IgG-S-S-Pyr) containing 2-pyridyl disulfide groups was prepared by the addition of N-succinimidyl 3-(2-pyridyldithio)-propionate (SPDP). The fluorescent conjugate (PE-S-S-IgG) was then formed by mixing PE-SH with IgG-S-S-Pyr. The product was analyzed by high pressure liquid chromatography (HPLC) on a Varian G3000SW column. This gel filtration column separates molecules primarily according to their hydrodynamic radii. PE-SH elutes 12 minutes after injection and IgG-S-S-Pyr elutes at about 13 minutes. See FIG. 1 showing the HPLC data. The reaction product PE-S-S-IgG emerges from the column at 8.5 minutes, much sooner than either reactant because the conjugate is larger than either component. The fluorescence emission of a 0.5 ml sample of this conjugate could readily be detected at a phycoerythrin conjugate concentration of less than $10^{-10}$ M.

EXAMPLE 2

A second example of the joining of a phycobiliprotein to another biomolecule is provided by the synthesis of a phycoerythrin-avidin conjugate. Avidin was activated by the addition of m-maleimidobenzoyl N-hydroxysuccinimide ester (MBS). The ester group of MBS reacted with nucleophiles on avidin. Sulfhydryl groups on thiolated phycoerythrin then reacted with maleimide groups on activated avidin molecules. Uncombined avidin was removed from the reaction mixture by chromatography on carboxymethyl-Sephadex.

EXAMPLE 3

A third example of the joining of a phycobiliprotein to another biomolecule is provided by an alternative route for the synthesis of a phycoerythrinavidin conjugate. Biotinylated phycoerythrin was prepared by reacting phycoerythrin with the N-hydroxysuccinimide ester of biotin. Avidin was added to biotinylated phycoerythrin to form a phycoerythrin-biotin-avidin conjugate (PE-B-A). Excess avidin was removed by gel filtration. PE-B-A, which binds very tightly to biotinylated molecules, was then used as a fluorescent stain in a fluorescence-activated cell sorting experiment. Biotinylated monoclonal antibody having specific affinity for immunoglobulin D (IgD) was added to a mixture of spleen cells. This monoclonal antibody combines with IgD molecules, which are present on the surface of about 40% of spleen cells. Excess antibody was removed by washing. PE-B-A was then added to this mixture of cells. The avidin unit of this highly fluorescent conjugate combined with biotin groups on cell surfaces bearing anti-IgG immunoglobulin. The fluorescence-activated cell sorter analysis of this cell population is shown in FIG. 2. The fluorescence intensity of cells labeled by the phycoerythrin conjugate is comparable to that obtained with a fluorescein conjugate in a parallel experiment. This finding demonstrates that phycobiliprotein conjugates are effective long wavelength fluorescent labels for fluorescence analyses of cells.

EXAMPLE 4

The phycoerythrin-biotin-avidin conjugate described above was also used to fluorescent-stain beads containing an antigen. Biotinylated monoclonal antibody having specific affinity for a target immunoglobulin was added to agarose beads (insoluble matrices) containing covalently attached target antigen. These beads were washed and PE-B-A was then added. Beads labeled with this fluorescent phycobiliprotein conjugate were examined by fluorescence microscopy. The labeled beads appeared yellow when viewed with a standard filter combination designed for fluorescein emission. With longer wavelength filters, the labeled beads appeared orange-red. A mixture of fluorescein-avidin labeled beads and PE-B-A labeled beads were also examined by fluorescence microscopy. The PE-B-A labeled beads could readily be distinguished from the fluorescein labeled beads because they were yellow rather than green (FIG. 3a) using fluorescein optics. With a longer wavelength set of filters, only the PE-B-A beads were brightly stained, in this case orange-red (FIG. 3b). These experiments show that phycobiliprotein-biomolecule conjugates are effective fluorescent stains for fluorescence microscopy.

EXAMPLE 5

Preparation of Phycobiliproteins

R-phycoerythrin was purified from red algae, *Gastroclonium coulteri* (Rhodymeniales), which were collected from Stillwater Cove, Monterey Peninsula, Calif. The fresh algal tissue was washed with distilled water, suspended in 50 mM sodium-phosphate buffer at pH 7.0, and blended for 3min at the highest speed setting of an Osterizer blender. The homogenate was filtered through several layers of cheese cloth and residual particulate matter removed by low speed centrifugation. The supernatant was brought to 60% of saturation with solid $(NH_4)_2SO_4$. All of the above steps were carried out at 4° C. The precipitate was collected by centrifugation, resuspended in 60% of saturation $(NH_4)_2SO_4$ in 50 mM sodium phosphate, pH 7.0, and slurried with DEAE-cellulose (microgranular; Whatman, Inc., Chemical Separation Div., Clifton, N.J.). The slurry was packed into a column. The column was developed stepwise with decreasing concentrations of $(NJ_4)_2SO_4$ in 50 mM sodium phosphate, pH7.0, down to 10% of saturation. At that point elution was completed with 200 mM sodium phosphate, pH7.0. The phycoerythrin eluted between 10% saturation $(NH_4)_2SO_4$ —50 mM sodium phosphate, pH7.0 and 200 mM sodium phosphate, pH7.0. The eluate was concentrated by $(NH_4)_2SO_4$ precipitation, re-dissolved in 50 mM sodium phosphate, pH7.0 and $(NH_4)_2SO_4$ added to 10% of saturation at 4° C. The protein crystallized under these conditions upon standing at 4° C.

*Synechococcus* 6301 C-phycocyanin (Glazer and Fang, Biol. Chem. (1973) 248:65–662) *Anabaena variabilis* allophycocyanin (Bryant et al, Arch. Microbiol. (1976) 110:61–75) and B-phycoerythrin (Glazer and Hixson, J. Biol. Chem. (1977) 252:32–42) were prepared as described in the references cited.

EXAMPLE 6

Preparation of Phycoerythrin-Avidin

A 50μl aliquot of 1 mg/ml N-hydroxysuccinimidobiotin (Sigma Chemical Co., St. Louis, Mo. or Biosearch, San Rafael, Calif.) in dimethylsulfoxide was added to 1ml of 2.7 mg/ml R-phycoerythrin (or B-phycoerythrin) in 50 mM sodium phosphate, pH 7.5 to give a reagent/phycoerythrin molar ratio of 13. The use of avidin and biotin in labeling studies has been described previously (Green, Adv. Protein Chem. (1975) 29:85–133; Heitzmann and Richards, PNAS USA (1974) 71:3537–3541). After 90min at room temperature, the reaction was quenched by the addition of 10μl of 100 mM glycyl-glycine, pH 7.5 and then dialyzed for 3 d at 4° C. against 50 mM sodium phosphate, pH 6.8 1ml of this mixture of biotinylated phycoerythrin (Biot-PE) and unmodified phycoerythrin was added slowly with stirring to 1ml of 5 mg/ml avidin in the same buffer. The molar ratio of tetrameric avidin to phycoerythrin was 20. This mixture of phycoerythrinavidin conjugates (PE-avidin), phycoerythrin, and avidin was fractionated by high-pressure liquid chromatography.

EXAMPLE 7

Preparation of Phycoerythrin-Immunoglobulin G (PE-IgG)

Thiolated phycoerythrin was prepared by the addition of 600μl of 15.5 mg/ml iminothiolane hydrochloride (Sigma Chemical Co.) (Jue et al., Biochemistry (1978) 17:5399–5406) to 1.2 ml of 3.6 mg/ml R-phycoerythrin in 125 mM sodium phosphate, pH 6.8. After 90min at room temperature, the reaction mixture was dialyzed overnight at 4° C. against 50 mM sodium phosphate, pH 6.8 and then for 2d against pH 7.5 buffer. Titration of an aliquot with 5,5'-dithiobis-(2-nitrobenzoic acid) showed that the average content of sulfhydryl groups per phycoerythrin molecule was 8.

A 30µl pf 1.1 mg/ml N-succinimidyl 3-(2-pyridylthio)-propionate (SPDP) (Pharmacia Fine Chemicals, Piscataway, NJ) (Carlsson et al., Biochem. J. (Tokyo) (1978), 173:723-737) in ethanol was added to 700µl of 4.2 mg/ml immunoglobulin G in 50 mM sodium phosphate pH 7.5. The immunoglobulin was a monoclonal $\gamma1$ mouse anti-allotype antibody having specificity for the a allotype of the mouse $\gamma2$a subclass. The molar ratio of SPDP to IgG was 5.3. The reaction was allowed to proceed for 2.5h at room temperature. Thiolated phycoerythrin (400µl of 1.7 mg/ml in the same buffer) was added to 500µl of this reaction mixture. The molar ratio of activated IgG to thiolated phycoerythrin was 4.7. After 12h at room temperature, 100µl of 80 mM sodium iodoacetate was added to block any remaining sulhydryl groups.

EXAMPLE 8

Preparation of Phycoerythrin-Protein A

To 0.5 ml B-phycoerythrin (4.08 mg/ml) in 0.1 M sodium phosphate-0.1 M NaCl, pH7.4, 10µl of SPDP in anhydrous methanol (2.65 mg SPDP/ml) was added to give an SPDP/protein molar ratio of 10. The reaction was allowed to proceed at 22° C. for 50min and was terminated by applying the reaction mixture to a column of Sephadex G-25 (1.0×17cm) equilibrated with 100 mM sodium phosphate-0.1 M NaCl, pH 7.4. The phycoerythrin peak, eluted with the same buffer, was collected and stored at 4° C.

To 0.5 ml protein A (Sigma Chemical Co.) from *Staphylococcus aureus*, 2 mg/ml in 100 mM sodium phosphate-100 mM NaCl, pH 7.4, 2.6µl of the above methanolic SPDP solution was added to give an SPDP/protein molar ratio of 9.5. After 40min at 22° C, the reaction was terminated by the addition of 25µl of 1 mM dithiothreitol in the pH 7.4 buffer. After 25min at 22° C, the reaction mixture was subjected to gel filtration as described above and the protein A peak collected.

Appropriate volumes of the phycoerythrin-S-S-pyridyl derivative and of the thiolated protein A were mixed to give a molar ratio of phycoerythrin to protein A of 1:2. The reaction mixture contained 0.77 mg phycoerythrin/ml and 0.27 mg of protein A/ml. After 6h at 22° C., the reaction mixture was stored at 4° C. and the phycoerythrin-protein A conjugate generated in this manner was used without further purification.

EXAMPLE 9

Preparation of Target Beads

IgG-Sepharose beads were prepared by adding 1.2 ml of 5.2 mg/ml IgG to 2 ml of a slurry of CNBr-activated Sepharose 4B (Pharmacia Fine Chemicals). The immunoglobulin was a mouse $\gamma2$a myeloma antibody of the a allotype. After 2h of end-over-end mixing at room temperature, the reaction was quenched by the addition of 2 ml of 1M glycine, pH 7.5. The beads were then washed exhaustively. Ovalbumin-Sepharose beads and avidin-Sepharose beads were prepared similarly. Biotin-Sepharose beads were prepared by reacting ovalbumin-Sepharose beads with N-hydroxysuccinimidobiotin.

Spectroscopic Measurement

Absorption spectra were obtained on a Beckman model 25 spectrophotometer (Beckman Instruments, Inc., Fullerton, Calif.). Fluorescence spectra were obtained on a Perkin-Elmer model 44B fluorometer equipped with DCSCU-2 corrected emission spectra unit, or on a Spex Fluorolog instrument. Fluorescence microscopy was carried out using a Zeiss Universal microscope with epiillumination optics.

High-pressure Liquid Chromatography

Coupling reactions were followed by high-pressure liquid chromatography on a Waters instrument with a Varian G3000SW gel filtration column which separates molecules primarily according to their hydrodynamic radii. For analyses, 20µg protein was applied in a volume of 10-20µl. In preparative experiments, 750µl of sample was applied and 400µl fractions were collected. The eluting-buffer was 200 mM sodium phosphate, pH 6.8 and the flow rate was 1 ml/min.

Fluorescence Staining of Lymphocytes

Human peripheral blood leukocytes were prepared using Ficoll-Hypaque gradients. Viability counts of the cells recovered were done by staining the cells with acridine orange and ethidium bromide and counting fluorescent cells with a fluorescence microscope using standard fluorescein optics. This dye combination stains live cells green and dead cells orange-red. Cell preparation were always >95% viable.

The anti-Leu antibodies used in this study were all monoclonally derived hybridoma antibodies (Becton, Dickinson & Co. Monoclonal Center, Mountain View, Calif.). The green fluorescence signal came from directly fluoresceinated antibodies. The red fluorescence signal came from biotinylated antibodies counterstained with phycoerythrin-avidin. Fluorescent antibody staining was done in one or two steps. Directly fluoresceinated antibodies were incubated with $10^6$ cells in 50µl of HEPES-buffered (10 mM) RPMI-1640 medium (deficient in phenol red and biotin) containing 5% (vol/vol) horse serum and 0.2% (wt/vol) azide for 20min on ice. The amount of antibody added had been previously determined to be optimal for staining this number of cells. For two-color staining, both the directly fluoresceinated antibody and the biotinylated antibody were incubated with $10^6$ cells in 50µl of medium for 20min on ice. After washing the cells twice with medium, the phycoerythrin-avidin conjugate was added to the cells in 50µl of medium. This mixture was incubated for an additional 20min on ice before finally washing the cells three times in medium. Cells were resuspended in 0.5 ml of medium for fluorescence analyses using the fluorescence-activated cell sorter.

Fluorescence-activated Cell Analyses

A modified Becton, Dickinson & Co. Fluorescence-activated Cell Sorter (FACS II) was used for fluorescence analyses of single cells. A 560 nm dichroic mirror divided the emission into a shorter wavelength component (the "green" channel) and a longer wavelength component (the "red" channel). Logarithmic amplifiers with a 3.5 decade logarithmic range were used for both channels Electronic compensation (Loken et al., J. Histochem. Cytochem. (1977) 25:899-907) corrected for fluorescein spillover into the red channel and for phycoerythrin spillover into the green channel. These corrected signals will be referred to as green and red fluorescence. The fluorescence data was displayed as contour maps which resemble topographic maps. The contour lines depict cell density on a linear scale. The number of cells in a region of the map is proportional to the volume represented by the contours in that region. The computer program that acquires and displays FACS data in this manner was written by Wayne Moore (Stanford University).

PE-avidin conjugate was prepared by biotinylating phycoerythrin and then adding an excess of avidin. An average of one biotin per phycoerythrin was incorporated when a 13-fold molar excess of N-hydroxysuccinimidobiotin was reacted with phycoerythrin for 90min. The reaction mixture obtained upon subsequent addition of a large excess of avidin was analyzed by high-pressure liquid chromatography. Phycoerythrin-avidin conjugates eluted first, followed by phycoerythrin and biotinylated phycoerythrin and then by avidin, as expected on the basis of their hydrodynamic radii. The reaction mixture contained a substantial amount of PE-avidin conjugates (peaks 1 and 2), in addition to phycoerythrin (peak 3) and avidin (peak 4). It seems likely that peak 2 corresponds to a conjugate containing one avidin molecule joined to one molecule of biotinylated phycoerythrin, whereas peak 1 and the region between peaks 1 and 2 consist of conjugates made up of three or more protein molecules. Fractions corresponding to peak 2 were collected and pooled. The major species is PE-avidin. Some unreacted phycoerythrin and a small amount of untreated avidin remained after this fractionation step. The capacity of this PE-avidin preparation for biotin was tested by adding it to biotin-Sepharose beads. These stained beads displayed intense orange-red fluorescence characteristic of phycoerythin. The prior addition of avidin to biotin-Sepharose beads, or of biotin to the PE-avidin conjugate, blocked the binding of PE-avidin to these beads, as evidenced by the fact that they appeared dark under the fluorescence microscope. Likewise, biotin-Sepharose beads stained with either phycoerythrin or biotinylated phycoerythrin did not fluoresce in the orange-red spectral region. These experiments, as well as the fluorescence-activated cell analyses to be discussed shortly, demonstrate that the PE-avidin conjugate binds specifically to biotin and biotinylated molecules. Furthermore, the quantum yield and emission spectrum of the PE-avidin conjugates are virtually the same as those of native phycoerythrin. A 1 ml sample of 10-12 M phycoerythrin (or phycoerythrin conjugate) excited at 520 nm gives a fluorescence signal at 576 nm that is twice as large as the Raman scattering at 631 nm from water. Thus, 10-15 mole of phycoerythrin in a standard fluorescence cuvet can readily be detected.

It is of interest to compare the fluorescence intensity of phycoerythrin with that of fluorescein. The fluorescence intensity of a dilute solution of a chromophore is proportional to $c\epsilon Q$, where c is the molar absorbance coefficient at the excitation wavelength, and Q is the fluorescence quantum yield. For excitation ar 488 nm (an argon-ion laser line): $\epsilon = 2.18 \times 10^6 cm^{-1} M^{-1}$ and $Q = 0.82$ for phycoerythrin; and $\epsilon = 8 \times 10^4 cm^{-1} M^{-1}$ and $Q = 0.9$ for fluorescein. Hence, a solution of phycoerythrin excited at 488 nm has a fluorescence intensity 14.5 as high as that of an equimolar solution of fluorescein. The observed intensity ratio depends also on the efficiency of the detection system with respect to emission wavelength. A phycoerythrin/fluorescein intensity ratio of 10 was measured when equimolar solutions of these substances were flowed through the cell sorter. It is estimated that $10^3$ molecules of phycoerythrin bound to a cell could be detected in flow cytometry experiments.

IgG-Sepharose beads displayed bright orange-red fluorescence after staining with the phycoerythrin-protein A conjugate, as anticipated, since protein A is known to bind to the $F_c$ portion of mouse 2a immunoglobulins. This staining of the beads was inhibited by the addition of the soluble IgG2a. Likewise, the conjugate of phycoerythrin with monoclonal anti-allotype antibody stained Sepharose beads containing covalently attached target immunoglobulin. These beads did not become fluorescent if soluble target immunoglobulin was added first to the phycoerythrin-antibody conjugate, or if soluble anti-allotype antibody was added first to the beads. Thus, the specific binding characteristics of the protein and of the anti-allotype antibody were retained in their conjugates with phycoerythrin.

The PE-avidin conjugate was used as the red-fluorescent stain in two-color fluorescence-activated cell analyses. The distribution of Leu antigens (OKT antigens) on the surface of human T-lymphocytes was investigated. (The identity of Leu and OKT antigens has recently been determined. Leu-1=OKT1; Leu-2=OKT8; Leu-3=OKT4; and Leu-4=OKT 3.) Leu-1 and Leu-4 are known to be present on all T-cells, whereas Leu-2a and Leu-2b are associated with suppressor and cytotoxic T cells, and Leu-3a and Leu-3b with helper and inducer T cells. The densities of Leu-1, Leu-2a, Leu-3b, and Leu-4 were determined by staining cells with a fluoresceinated antibody specific for one of these antigens and measuring green fluorescence of these cells. The density of Leu-3a was ascertained by staining T-lymphocytes with biotinylated antibody specific for Leu-3a, followed by PE-avidin, and measuring the red fluorescence. In a control experiment, the cells were stained with PE-avidin, but not antibody. The peak near the origin of this plot arises from the autofluorescence of these cells, inasmuch as unstained cells give the same pattern. Thus, PE-avidin has virtually no affinity for these cells. The result of staining these cells with fluoresceinated anti-leu-3b was two peaks, one near the origin arising from cells ($\sim$50%) devoid of Leu-3b on their surface, and the other coming from cells ($\sim$50%) expressing Leu-3b. The green signal is 50 times as bright as the autofluorescence of the Leu-3b negative cells, whereas their red signals are the same. The converse result, was obtained when T-lymphocytes were stained with biotinylated anti-Leu-3a, followed by PE-avidin. The red fluorescence of cells containing Leu-3a on their surface is 30 times as high as that of negative cells, whereas the green signals of these two populations are the same. The result of a simultaneous analysis for Leu-3a and Leu-3b is a peak near the origin arising from cells that express neither antigen, and another peak which comes from cells that contain both Leu-3a and Leu-3b. In other words, every cell that expresses Leu-3a also expressed Leu-3b, and vice versa. This binding is expected, because 3a and 3b are known to be nonoverlapping determinants on the same protein molecule.

Two-color fluorescence-activated cell analyses of the distribution of Leu-3a relative to Leu-1, Leu-2a, and Leu-4 on human peripheral blood lymphocytes were also carried out. The observed Leu 1 staining pattern indicates that $\sim$60% of peripheral blood lymphocytes from this donor are T-cells because the Leu-1 antigen is known to be present on all human peripheral T-cells. The profile obtained by also staining for Leu-3a shows that not all T-cells bear the Leu-3a antigen. About 80% of the T-cells carry Leu-3a and Leu-1. These doubly-positive cells include the helper and inducer T-cell subpopulations. A different result was obtained for the distribution of Leu-2a and Leu-3a. Only 10% of all lymphocytes analyzed express Leu-2a an antigen known to be associated with the suppressor and cytotoxic T-cell subpopulations. The profile for Leu-2a and Leu-3a demonstrates that a T-cell expresses Leu-2a or Leu-3a but not both antigens. This mutual exclusion is in harmony with the fact that a particular T-cell may be either a suppressor-cytotoxic or a helper-inducer cell, but not both. The distribution of Leu-4 is similar to that of Leu-1, as expected because Leu-4 is known to be present on all human peripheral T-cells. In staining for Leu-3a and Leu-4 all cells that were found positive for Leu-3a are also positive for Leu-4.

The above data demonstrate that biliprotein conjugates are a valuable class of fluorescent reagents for analyses of molecules. The fluorescence-actived cell sorter examples are specific evidence of the utility and variety of analyses which one can carry out employing the biliproteins. The high extinction coefficient of phycoerythrin at 488 nm, the position of an argon-ion laser line, makes it possible to simultaneously excite fluorescein and phycoerythrin with high efficiency. Their fluorescence emission maxima lie at 515 and 576 nm, respectively, and so their emission contributions can readily be separated by appropriate filters. An advantage of using phycoerythrin is that a single laser line suffices for two-color analyses.

The phycobiliprotein conjugates open up a possibility of carrying out three-parameter analyses with two laser sources. For example, allophycocyanin could serve as the third fluorescent chromophore. In such a three-color experiment, fluorescein and phycoerythrin could be excited by the 488 nm argon-ion line and allophycocyanin by the 625 nm output of a dye laser (or by a krypton or helium-neon laser). The absorption and emission spectra of phycobiliproteins point to the possibility of four-color analyses if C-phycocyanin conjugates were also employed. The phycobiliproteins are well suited for fluorescence immunoassays. The fluorescence of femtomole quantities of phycobiliproteins such as phycoerythrin can readily be detected. Furthermore, background fluorescence from body fluids and supporting media, diminishes markedly in going to the red end of the spectrum. The orange-red emission of phycobiliproteins is particularly advantageous in this regard. Furthermore, the phycobiliproteins can be conjugated to a wide variety of ligands and receptors without interfering with the functioning of the ligand or receptor in specific binding pairs, nor losing the desired spectral properties of the phycobiliproteins.

Although the foregoing invention has been described in some detail by way of illustration and example for purposes of clarity of understanding, it will be obvious that certain changes and modifications may be practiced within the scope of the appended claims.

What is claimed is:

1. A receptor covalently bound to a phycobiliprotein.
2. A receptor according to claim 1, wherein said receptor is a cell surface protein receptor.
3. A receptor according to claim 1, wherein said receptor is avidin.
4. A receptor according to claim 1, wherein said receptor is an immunoglobulin.

* * * * *

UNITED STATES PATENT AND TRADEMARK OFFICE
CERTIFICATE OF CORRECTION

PATENT NO. : 5,055,556

DATED : October 8, 1991

INVENTOR(S) : Lubert Stryer; Alexander N. Glazer; Vernon T. Oi

It is certified that error appears in the above-indentified patent and that said Letters Patent is hereby corrected as shown below:

Column 1, line 14, insert the following information:

--This invention was made with Government support under NSF Grant No. PCM 79-10996 and NIH Grant Nos. GM-24032 and AI-06144. The Government has certain rights in this invention.--

Signed and Sealed this

Fifteenth Day of November, 1994

*Attest:*

BRUCE LEHMAN

*Attesting Officer*     *Commissioner of Patents and Trademarks*